(12) United States Patent
Arlt

(10) Patent No.: US 6,787,676 B2
(45) Date of Patent: Sep. 7, 2004

(54) PROCESS FOR THE PREPARATION OF NON-CHIRAL AND OPTICALLY ACTIVE ORGANIC COMPOUNDS CONTAINING HYDROXYL GROUPS

(75) Inventor: Dieter Arlt, Lemgo (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 10/066,979

(22) Filed: Feb. 4, 2002

(65) Prior Publication Data

US 2002/0111515 A1 Aug. 15, 2002

(30) Foreign Application Priority Data

Feb. 5, 2001 (DE) .......................................... 101 05 104

(51) Int. Cl.$^7$ ............................................. C07C 33/34
(52) U.S. Cl. ...................... 568/808; 502/155; 502/158; 502/159; 568/814
(58) Field of Search ................................ 568/808, 814; 502/155, 158, 159

(56) References Cited

U.S. PATENT DOCUMENTS

| | | | |
|---|---|---|---|
| 5,244,857 A | 9/1993 | Pugin et al. ............... | 502/167 |
| 5,252,751 A | 10/1993 | Pugin et al. ............... | 549/214 |
| 5,306,853 A | 4/1994 | Pugin et al. ............... | 585/269 |
| 5,308,819 A | 5/1994 | Pugin et al. ............... | 502/162 |
| 5,382,729 A | 1/1995 | Pugin et al. ............... | 585/277 |
| 5,432,289 A | 7/1995 | Pugin et al. ............... | 549/221 |
| 5,457,219 A | 10/1995 | Foricher et al. ........... | 556/404 |
| 5,763,688 A | 6/1998 | Ikariya et al. .............. | 568/814 |
| 5,935,892 A | 8/1999 | Davis et al. ............... | 502/156 |
| 5,990,318 A | 11/1999 | Chan et al. ................ | 548/412 |
| 6,162,951 A | 12/2000 | Polywka et al. ............ | 568/13 |

FOREIGN PATENT DOCUMENTS

| | | |
|---|---|---|
| CA | 2170100 | 8/1996 |
| WO | 01/74828 | 10/2001 |

OTHER PUBLICATIONS

Ohkuma, Adv. Synth. Catal., vol. 343(4), pp. 369–375 (Apr., 2001).*
AN 1999: 760462.
AN 1994: 557248.
AN 1998: 715053.
J. Am. Chem. Soc., (month unavailable) 1999, 121, pp. 7407–7408, Highly Effective Soluble Polymer–Supported Catalysts for Asymmetric Hydrogenation by Qing–hua Fan, Chang–Yu Ren, Chi–hung Yeung, Wen–hao Hu and Albert S. C. Chan.
J. Org. Chem, (month unavailable) 1994, 59, pp. 3064–3076, Cationic BINAP–Ru(II) Halide Complexes: Highly Efficient Catalyst for Stereoselective Asymmetric Hydrogenation of α– and β–Funtionalized Ketones by Kazushi Mashima, Koh–hei Kusano, Naomasa Sato, Yoh–ichi Matsumura, Kyoko Nozaki, Hidenori Kumobayashi, Noburu Sayo, Yoji Hori, Takero Ishizaki, Susumu Akutagawa, and Hidemasa Takaya.

J. Org. Chem., (month unavailable) 1998, 63, pp. 3137–3140, Preparation and Use of a Polymer Supported BINAP Hydrogenation Catalyst by D. J. Bayston, J. L. Fraser, M. R. Ashton, A. D. Baxter, M. E. C. Polywka, and E. Moses.

Tetrahedron: Asymmetry, vol. 2, No. 7, pp. 555–567, (month unavailable) 1991, Asymmetric Synthesis. Practical Production of D and L Threonine. Dynamic Kinetic Resolution in Rhodium and Ruthenium Catalyzed Hydrogenation of 2–Acylamino–3–Oxobutyrates by J. P. Genet, C. Pinel, S. Mallart, S. Juge, S. Thorimbert and J. A. Laffitte.

Tetrahedron Letters, vol. 34, No. 12, pp. 1905–1908, (month unavailable) 1993, Preparation of Primary Vicinal Diamines from Amino Acid Esters and Crystal Structure of a Chiral Nickel Salen Complex by Shiow–Jyi Wey, Kenneth J. O'Connor and Cynthia J. Burrows.

Journal of Molecular Catalysts A: Chemical 107, (month unavailable) 1996, pp. 273,279, Immobilized catalysts for enantioselective hydrogenation: The effect of site–isolation by B. Pugin.

Synlett, No. 5, (month unavailable) 2000, pp. 680–682, Poly–NAP as Ligand for the Asymmetric Hydrogenation of Ketones by Rob ter Halle, Emmanuelle Schulz, Michel Spagnol and M. Lemaire.

Tetrahedron Letters, 41, (month unavailable) 2000, pp. 643–646, 'Diam–BINAP'; a highly efficient monomer for the synthesis of heterogeneous enantioselective catalylsts by Rob ter Halle, Benoist Colasson, Emmanuelle Schulz, Michel Spagnol and M. Lemaire.

Abdur–Rashid K et al: "Ruhcl(disphospine)(diamine): Catalyst precursors for the stereoselective hydrogenation of ketones and imines" Organometallics, ACS, Columbus, OH, US, Bd. 20, Nr. 6, 19. Mar. 19, 2001, Seltn 1047–1049, XP001033320 ISSN:0276–7333, Abbildung 1, Seite 1047, rechte Spalte Seite 1048, rechte Spalte; Tabelle 1.

Doucet H et al: "Trans–Ärucl2(phosphane)2(1,2–Diamine)Ü and Chiral Trans–Ärucl2(disphophane) (1,2–diamine): Shelf–stable precatalysts for the rapid, productive, and stereoselective hydrogenation of ketones" Angewandte Chemie. International Edition, Verlag Chemie. Weinheim, DE, Bd. 37.37, Nr. 12, 1998, Seiten 170–3–1707, XP002938991 ISSN: 0570–0833 das ganze Document.

* cited by examiner

*Primary Examiner*—Michael L. Shippen
(74) *Attorney, Agent, or Firm*—Norris McLaughlin & Marcus, PA

(57) ABSTRACT

Non-chiral and, in particular, optically active alcohols are prepared from a carbonyl compound with hydrogen in the presence of a catalyst, a base and optionally a diamine in an advantageous manner by using a catalyst that contains both a support-bonded Ru(II) complex bisphosphine ligand and a diamine ligand.

7 Claims, No Drawings

PROCESS FOR THE PREPARATION OF NON-CHIRAL AND OPTICALLY ACTIVE ORGANIC COMPOUNDS CONTAINING HYDROXYL GROUPS

Organic compounds containing hydroxyl groups, including those in optically active form, are important intermediates, for example for the preparation of pharmaceutical active ingredients, crop protection agents, fragrances and liquid-crystalline substances.

EP-A 718 265 discloses a process for the preparation of non-chiral and optically active alcohols in which a carbonyl compound is reacted with hydrogen in the presence of a homogeneous catalyst, a base and an organic compound containing nitrogen. The homogeneous catalyst may, for example, be a ruthenium complex containing phosphine ligands, the base may be an alkali metal or alkaline earth metal hydroxide, and the organic compound containing nitrogen may be an amine.

A disadvantage of this process is the use of a homogeneous catalyst, which hinders work-up of the reaction mixture and the preparation of products which are not contaminated with catalysts or constituents thereof. Furthermore, the isolation of the valuable catalyst or its constituents is possible, if at all, only with high technical complexity and expenditure. Finally, it is difficult to carry out processes using homogeneous catalysts in a continuous manner.

Homogeneous catalysts are characterized by high selectivities and activities which are not generally achieved by corresponding heterogeneous catalysts.

It therefore had to be taken into consideration that in the present case as well, when transferring from homogeneous to heterogeneous catalysts, any advantages, e.g. with regard to work-up of the reaction mixture, purity of the product prepared, catalyst recovery and continuous reaction procedure, can only be realised in conjunction with serious disadvantages, e.g. with regard to selectivity and activity.

We have now found a process for the preparation of non-chiral and optically active alcohols in which a carbonyl compound is reacted with hydrogen in the presence of a catalyst, a base and optionally a diamine, which is characterized in that the catalyst used is a support-bonded Ru(II)-phosphine-diamine-Ru complex catalyst of the formula (I).

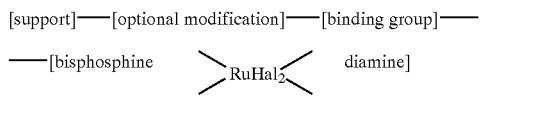

Hal=Cl or Br    (I)

A short time ago (Synlett 2000, No. 5 680–682), a process for the asymmetric hydrogenation of ketones became known which is carried out using a heterogeneous catalyst component which contains BINAP structural elements incorporated in the main chain. This is an oligomeric diisocyanate adduct with the name "poly-NAP" (see Tetrahedron Letters 41 (2000), 643–646), which is significantly different from the catalysts used according to the invention which contain support-bonded bisphosphine-diamine-Ru(II) complexes. The support-bonded catalysts used according to the invention are, for example in contrast to poly-NAP, insoluble in all solvents. A significant advantage of the process according to the invention is that, because of the multiplicity of chiral bisphosphines which are suitable for constructing support-bonded catalysts, a large number of different heterogeneous bisphosphine components can be provided in order, in combination with the amine components of the catalyst system, to achieve the optimum processing method for the substrate in question.

Catalysts which contain support-bonded bisphosphine ligands and which are suitable as precursors for the novel catalysts used according to the invention are known or can be obtained analogously to the preparation of ones which are known (see e.g. J. Org. Chem. 63, 3137 (1998), GB-A 96-19684, EP-A 496 699, EP-A 496 700, EP-A 728 768, J. Mol. Catal. A 107 (1–3), 273 (1996) and 13th International Conference on Org. Synth., Warsaw, July 1–5, 2000, Book of Abstracts, PB-4, p. 227).

A process for the preparation of non-chiral alcohols using such catalysts in the presence of amines and a base has not, however, hitherto been considered.

According to the invention, alcohols are obtained by reacting a carbonyl compound with hydrogen in an advantageous manner if the hydrogenation is carried out using a catalyst of the formula (I) in the presence of a base.

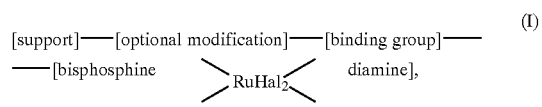    (I)

where
Hal is chlorine or bromine.

It is also possible to carry out the hydrogenation using a support-bonded, insoluble catalyst of the formula (II) if both a base and also a diamine are present in the reaction mixture at the same time during the hydrogenation. In this case, a catalyst of the formula (I) is formed in situ.

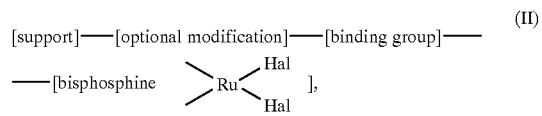    (II)

where
Hal is chlorine or bromine.

Preference is, however, given according to the invention to using catalysts of the formula (I) which already contain support-bonded Ru(II) complexes which, in each case contain both bisphosphine and also diamine ligands.

Suitable supports for He catalyst to be used according to the invention are inorganic materials, e.g. silica gels, and organic materials, e.g. crosslinked polymers.

Examples of inorganic supports which may be mentioned are: silicates or metal oxides in powder form with an average particle size between 10 nm and 2000 µm, preferably 10 nm and 500 µm. The particles may either be compact or porous, in the latter case the internal surface area being between 1 and 1200 m². Examples of oxidic supports which may be mentioned are $SiO_2$, $TiO_2$, $ZrO_2$, MgO, $WO_3$, $Al_2O_3$, and $La_2O_3$, and examples of silicates are silica gels, aluminas, zeolites and porous glass (controlled pore glass). Preferred supports are silica gels and aluminium oxides.

Organic catalyst supports are, for example, crosslinked bead polymers which can be obtained by suspension polymerization with the addition of bifunctional monomers from styrene, acrylates or methacrylates or (meth)acrylamides.

In order to permit a binding of the bisphosphine ligands, these supports must contain reactive groups. Suitable for this purpose are, for example, primary and secondary amino groups, hydroxyl, carboxyl and isocyanate groups, and groups which contain reactive halogen, such as benzylic chlorine or bromo(ar)alkyl.

Such groups can be introduced as early as during the preparation of the bead polymer using functional comonomers such as acrylic acid, methacrylic acid, 2-hydroxyethyl acrylate, 2-methyl-2-isocyanato-propyl acrylate or by subsequent modification of the support, e.g. by chloromethylation of the crosslinked polystyrene bead polymer, which may optionally be followed by a further functionalization, such as, for example, saponification and polyether grafting. The preparation of such polymers with reactive groups is known.

It has proven advantageous to arrange the modification of the support such that a greater distance is maintained between support and bisphosphine, a spacer being advantageous which consists of an alkylene or aralkylene or an alkyleneoxy chain optionally with incorporated ester, ether, amide, urethane or urea groups and includes at least 12 atoms between support and bisphosphine.

The inorganic support—in particular silica gels—can be modified in a manner known per se by reaction with silicic esters or chlorosilanes which each contain suitable functional groups, in order to introduce reactive groups suitable for the desired linking, such as, for example, amino groups. Examples of compounds suitable for such a modification which may be mentioned are 3-aminopropyl-triethoxysilane, trichlorovinylsilane and 3-mercaptopropyl-triethoxysilane.

It is also possible to react the inorganic support with suitable modified bisphosphine derivatives directly to give the fixed bisphosphine (derivatives) according to the invention. For this modification, bisphosphine derivatives are used which contain functional groups of the formula

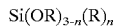
$$Si(OR)_{3-n}(R)_n$$

or

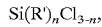
$$Si(R')_n Cl_{3-n},$$

where
R is alkyl,
R' is alkyl or alkoxy and
n is 0–2.

The reaction takes place analogously to known modifications of silica gels with chlorosilanes or silicic esters.

For the preparation of the catalysts used according to the invention, chelate-forming bisphosphines are used which contain functional groups which can generate a covalent bond with reactive groups on a suitable if suitably modified, insoluble support.

Examples of functional groups of the bisphosphine derivatives used for linking with the reactive groups of the above-described, optionally correspondingly modified supports which may be mentioned are: aromatically or (ar) aliphatically bonded primary or secondary amino groups, aromatically or (ar)aliphatically bonded hydroxyl groups, carboxyl and isocyanate groups, and aromatically bonded chloromethyl and chlorosulphonyl groups.

(Co)polymerizable groups, such as, for example, aromatic vinyl groups, (meth)acrylate or (meth)acrylamide groups are particularly suitable.

The linking can be carried out either with correspondingly functionalized bisphosphines and also with the analogous bisphosphine oxides. If chlorosulphonyl or chloromethyl groups are used, the procedure on the bisphosphine oxide stage is obligatory in order to avoid secondary reactions.

In the case of linking with the polymeric support on the phosphine oxide stage, it is necessary to subsequently reduce the support-bonded bisphosphine oxide in a manner known per se using silanes in the presence of tertiary amines to give the polymer-bonded bisphosphine.

Correspondingly, for example, bindable functional-group-containing derivatives of 1,2-bis(diphenylphosphino-)ethane, 1,2- and 1,3-bis(diphenylphosphino-)propane, (phenylene-1,2-diyl)bis(diphenylphosphine), pyrrolidin-3,4-diyl)-bis(diphenylphosphine) (unmodified) are used, and, in particular for the preparation of enantioselectively effective catalysts, derivatives with bindable functional groups of the chirally uniform chelating bisphosphines Dipamp, Prophos, Norphos, Chiraphos, Deguphos (unmodified), Diop, ModDiop, Bppm, ModBppm, Duphos and BppfOH (unmodified) are used (for the abbreviations see Handbook of Enantioselective Catalysis, Ed. H. Brunner, W. Zettlmeier, VCH Verlap Weinheim, 1993).

Particular preference is given to using derivatives of atropisomeric bisphosphines which contain groups suitable for the linking, in particular those in chirally uniform form, as building blocks for the catalysts according to the invention. Examples which may be listed here are enantiomerically pure derivatives, containing bindable functional groups, of 2,2'-bis(diarylphosphino)-1,1'-binaphthylene, such as 5,5'-diamino-2,2'-bis(diphenylphosphino)-1,1'-binaphthyl, 7,7'-dihydroxy-2,2'-bis(di-(m-xylyl)phosphino)-1,1'-binaphthyl, 4-(2,2'-bis(diphenylphosphino)-1,1'-binaphth-6-yl)butanoic acid, 4-(2,2'-bis(diphenylphosphino)-1,1'-binaphth-6-yl)butanol, or derivatives, containing groups able to link with suitable supports, of at least in 6,6'-position-substituted (biphenyl-2,2'-diyl)bis(diarylphosphines), biphenyl-2,2'-diyl)-bis(dicycloalkylphosphines) or (biphenyl-2,2'-diyl)bis(dihetarylphosphines), such as, for example, (6,6'-dihydroxybiphenyl-2,2'-diyl)bis(diphenylphosphine), (6-hydroxy-6'-methoxybiphenyl-2,2'-diyl)bis(di-(m-xylyl)phosphine, (6,6'-dihydroxy-biphenyl-2,2'-diyl)bis(dicyclohexylphosphine) and (6,6'-dihydroxybiphenyl-2,2'-diyl)bis(dithien-2-ylphosphine).

Optionally modified support material and modified phosphine are then combined such that both components can form a chemical bond with one another. One component may contain, for example, COOH groups and the other component may contain $NH_2$ groups, which can react with one another to form —CO—NH bonds.

Depending on the combination of reactive groups chosen, various types of bonds can be realised, e.g. as well as —CO—NH—, also —CO—NR—, CO—O—, —O—, —OCONH—, —NH— CO—NH, —O—CO—NR— and —O—CO—O—. The methods of coupling correspondingly reactive substances to supports are known.

A particularly preferred linking method consists in carrying out a free-radical polymerization of a bisphosphine (oxide) which has a polymerizable group in the presence of a silica gel which contains SH groups.

Such SH-group-containing silica gels are known and are obtained by modification of base silica gels, e.g. by reaction with 3-mercaptopropyl-trimethoxysilane under acidic catalysis.

In this procedure, the coverage density of the particle surface with catalyst groups can be readily controlled via the easily adjustable content of SH groups on the support material. At the same time, using this method, it is possible, even with a polymerization reaction, to obtain a high binding yield, based on monomeric bisphosphine (oxide) used, and a high coverage density of fixed ligands. Heterogeneous complex catalysts prepared in this way are further characterized in that by high pressure stability, which is an important property primarily for use in continuous processes.

Suitable compounds for this type of preparation of the novel catalysts for the process according to the invention are bisphosphine (oxide)s with polymerizable groups, in particular those monomers $M^1$ likewise included by the invention, which are described below according to the formula:

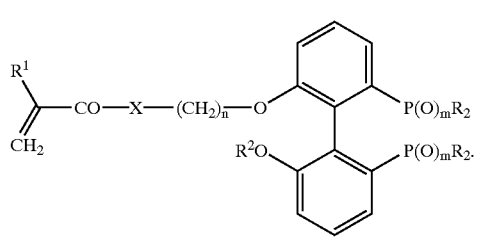

(M¹)

In the formula $M^1$

R is phenyl, 2- or 3- or 4-methylphenyl, 3,5-dimethylphenyl, 3,5-dimethyl-4-methoxyphenyl, 3,5-di-tertbutylphenyl or cyclohexyl, $R^1$ is hydrogen or methyl, X is O or NH, $R^2$ is methyl, ethyl, n- or isopropyl; n- or isobutyl, n-pentyl, n-hexyl, cyclohexyl, n-heptyl or n-octyl, n is a number from 2 to 12, m is zero or 1, preferably 1.

The preparation of a bisphosphine oxide described by the formula $M^1$ (where m=1) takes place, for example, according to Scheme 1:

Scheme 1

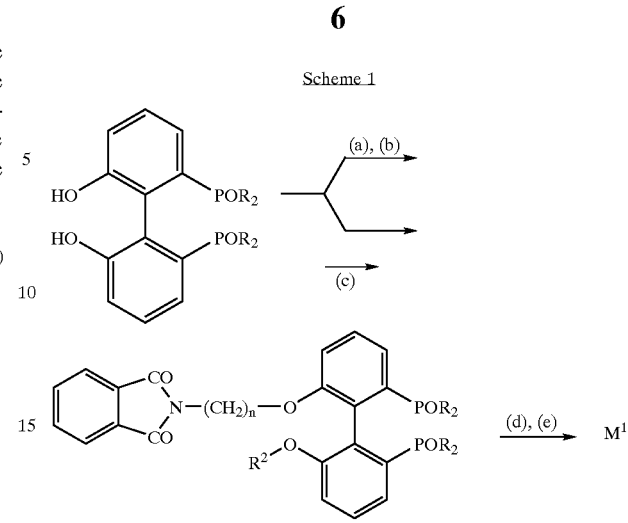

(a): $R^1$-Hal (Hal=Br, I)/$K_2CO_3$/DMF, 80° or N-ω-Br-alkyl-phthalimide/$K_2CO_3$/DMF, 80°

(b): N-ω-Bromoalkyl-phthalimide/$K_2CO_3$/DMF, 80° or $R^1$-Hal(Hal=Br, I)

(c): N-ωBromoalkyl-phthalimide/$R^1$-Hal(Hal=Br, I)/$K_2CO_3$/DMF, 80°

(d): $N_2H_4$, EtOH, reflux/HCL, $H_2O$ (e): $CH_2$=CRlCOCl/NaOH/$C_2Cl_2H_2O$.

Both synthesis alternatives can be used, preference being given to the single-stage, mixed alkylation (c).

A further preferred group of monomers is derived from novel bisphosphine (oxides) of the formula $M^3$, the preparation and further reactions of which are depicted in Scheme 2.

Scheme 2

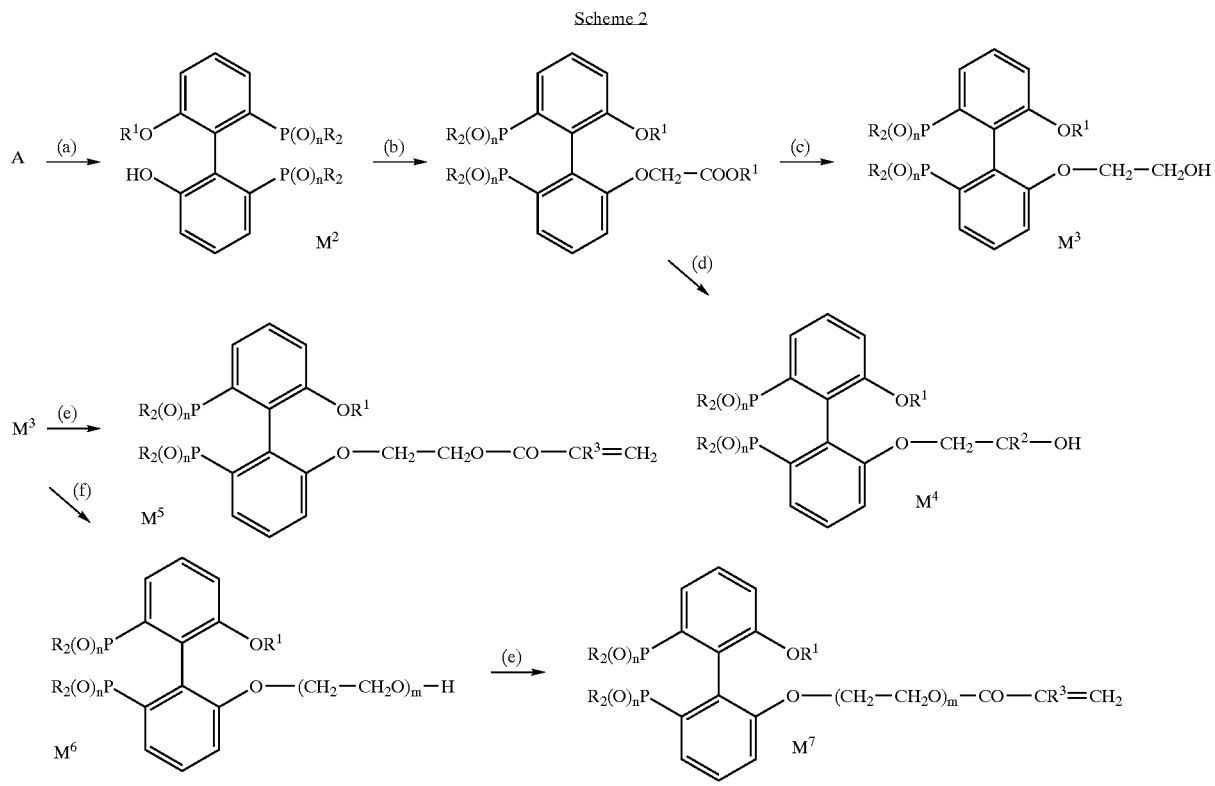

-continued

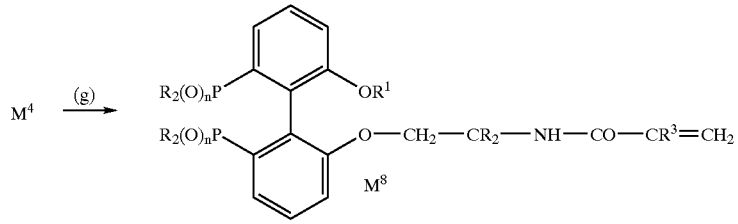

A is in Scheme 2 (R)- or (S)-(6,6'-dihydroxy-biphenyl-2,2'-diyl)bis(diphenylphosphine) or bisphosphine oxides thereof, preferably bisphosphine oxides.

In the formulae of Scheme 2,

R is phenyl, 2- or 3- or 4-methylphenyl, 3,5-dimethylphenyl, 3,5-dimethyl-4-methoxyphenyl, 3,5-ditert-butylphenyl or cyclohexyl, $R^{1'}$, $R^1$ and $R^2$, independently of one another are $C_1$- to $C_8$-(cyclo)alkyl, such as methyl, ethyl, n- or isopropyl, n-, i- or sec-butyl, 2,2-dimethyl-1-butyl, cyclohexyl, n-heptyl and n-octyl.

$R^3$ is H or $CH_3$, n is 1 or zero, m is 2–100, preferably 2–60.

Legend for Scheme 2:
(a): $R^1Br/K_2CO_3/DMF$, 80°;
(b): $BrCH_2COOR^3/K_2CO_3/DMF$, 80°;
(c): $LiAlH_4$, THF/optionally followed by $H_2O_2$, $CH_2Cl_2$;
(d): $R^2MgX$ (X=Br or I), THF;
(e): $CH_2=CR^3COCl$, base
(f): Ethylene oxide, $R^1ONa$(cat.);
(g): $CH_2=CR^3CN$, $H_2SO_4$.

The compounds of the general formulae $M^1$, $M^2$, $M^3$, $M^4$, $M^5$ and $M^6$ are likewise covered by the invention.

The polymerizable monomers $M^5$ and $M^6$ are in each case mixtures of diastereomers which, as a result of the described linking with correspondingly functionalized supports, lead to valuable catalysts which are used in the process according to the invention.

If desired, these mixtures can be separated into the individual stereoisomers by known processes, e.g. by tractional crystallization or by chromatographic means, and be converted into the corresponding catalysts.

The bridged bisphosphine oxide of the formula $M^2$ is a valuable intermediate which can be converted, by epoxidation or dihydroxylation, into correspondingly functionalized derivatives which, after linking with suitable supports, e.g. reactive resins containing amino or carboxyl groups, lead to catalysts according to the invention.

In a similar way, the bisphosphine oxides containing amino groups $M^9$ and $M^{10}$ can be used. It may be advantageous to use the corresponding bisphosphines $M^{10}$ and $M^9$, which are likewise covered by the invention, for the linking with correspondingly functionalized supports because the monomeric bisphosphines accessible in a known manner by reduction with trichlorosilane can be used in a more diverse manner than a phosphine fixed in a certain way.

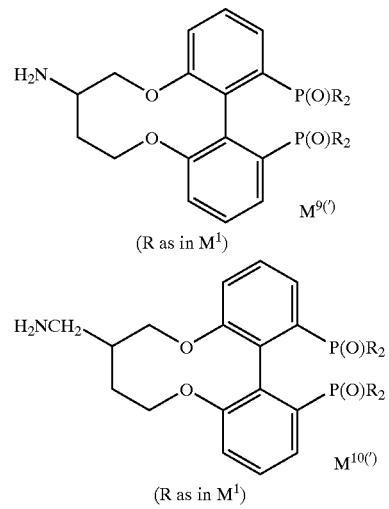

It has been found that not only catalysts of the formula (I) which contain the building blocks $M^9$ or $M^{10}$ are excellent catalysts for the enantioselective hydrogenation of (simple) ketones, but rather also that their precursors of the formula (II) can surprisingly be used as outstandingly selective and active hydrogenation or isomerization catalysts for other substrates, such as, for example, β-ketocarboxylic esters, α,β-unsaturated carboxylic acids or certain alkylamines in a process known per se.

The bisphosphines are then bonded to a support.

It is stated that any combination of preferences given are also covered by the invention.

In order to obtain heterogeneous Ru(II)-phosphine complex catalysts of the formula (II) to be used according to the invention, the phosphines bonded to a support can be reacted with suitable Ru(II) complexes. The Ru(II) complexes used for this purpose are, for example, the complexes of the formula

[Ru(aren)X_2]_2, in which
X is Cl or Br,
such as, for example, (p-cymene)-ruthenium(II) chloride, dimer, (see J. Org. Chem., 59, 3064, 1994). In particular, bis-(2-methallyl-cyclooctyl-1,5-diene-Ru(II) complex is suitable for the preparation of catalysts of the formula (II) (see Tetrahedron: Asymmetry, Vol. 2, No. 7, p. 565, 1991).

To prepare catalysts of the formula (I), for examples the heterogeneous precursor of the formula (II) is suspended in solutions of the diamine. The solvents used for this purpose are, for example, dichloromethane, acetonitrile or DMF. 1 to 10 equivalents of the diamine based on Ru are used in dilate solution, and the reaction is for example carried out under a protective gas, preferably argon, at temperatures of from 20° to 100° C. over the course of from about 3 to 48 hours. The catalyst of the formula (I) filtered off under a protective gas and washed out is dried under reduced pressure and is storage-stable.

Suitable carbonyl compounds for use for the process according to the invention are, for example, those of the formula (V)

$$R^1\text{—CO—}R^2 \qquad (V),$$

in which

R$^1$ and R$^2$ may be identical or different and are in each case hydrogen, straight-chain or branched $C_1$–$C_{12}$-alkyl, $C_2$–$C_{12}$-alkenyl or $C_2$–$C_{12}$-alkenyl, are $C_2$–$C_8$-cycloalkyl, $C_6$–$C_{12}$-aryl or $C_4$–$C_{11}$-heteroaryl having in each case 1 to 3 ring heteroatoms from the groups N, O or S.

Alkyl, alkenyl, alkenyl and cycloalkyl radicals can optionally be substituted by halogen, hydroxyl, di-$C_1$–$C_{12}$-alkylamino, ($C_6$–$C_{10}$-aryl-$C_1$–$C_{12}$-alkylamino, di-$C_6$–$C_{10}$-arylamino, $C_1$–$C_{12}$-alkoxy, $C_1$–$C_{12}$-alkoxycarbonyl, amide and/or urethane groups, where, for example, up to 3 identical or different substituents may be present.

Aryl and heteroaryl radicals can optionally be substituted by $C_1$–$C_{12}$-alkyl, di-$C_1$–$C_{12}$-alkylamino-$C_1$–$C_{12}$-alkyl, halogen-$C_1$–$C_{12}$ alkyl, hydroxy-$C_1$–$C_{12}$-alkyl, $C_2$–$C_{12}$-alkenyl, $C_2$–$C_{12}$-alkenyl, halogen, $C_1$–$C_{12}$-alkoxy, halogen-$C_1$–$C_{12}$-alkoxy, $C_6$–$C_{10}$-aryloxy, hydroxyl, carboxyl, $C_1$–$C_{12}$-alkoxycarbonyl, amide and/or urethane groups, where, for example, up to 3 identical or different substituents may be present.

R$^1$ and R$^2$ can together with the CO group in between also form a cyclo-$C_4$–$C_{12}$-alkyl ketone, where the cycloalkyl moiety may be substituted as given above for R$^1$=alkyl, and may also be unsaturated.

The alkyl groups, including those in combined radicals, are preferably $C_1$–$C_6$-alkyl groups. The alkenyl and alkenyl groups, including those in combined radicals, are preferably $C_2$–$C_4$-alkenyl or $C_2$–$C_4$-alkenyl groups.

The cycloalkyl groups, including those in combined radicals, are preferably $C_4$–$C_7$-cycloalkyl groups.

The aryl groups, including those in combined radicals, are preferably $C_6$–$C_{10}$-aryl groups, and the heteroaryl groups are preferably those which contain 5 to 9 ring carbon atoms.

The alkoxy groups in combined radicals are preferably $C_1$–$C_6$-alkoxy groups.

Halogen in combined radicals is preferably fluorine or chlorine.

Particularly preferred alkyl groups are:
methyl, ethyl, propyl, isopropyl, n-butyl, isobutyl, tert-butyl, sec-butyl, pentyl, hexyl, heptyl, chloromethyl, 2-chloroethyl, 2-hydroxyethyl, 2-dibenzylaminoethyl, 2-(N-benzyl-N-methylamino)-ethyl, 2-ethoxyethyl, methoxycarbonylmethyl, 2-(N-methyl-N-methoxycarbonylamino)-ethyl, vinyl, methallyl, propionyl, cyclopropyl, cyclobutyl, cyclopentyl, cyclohexyl, 2-methyl-cyclohexyl, benzyl, pyridyl-2-methyl and (5-trifluoromethyl-pyridyl-2)-methyl.

Particularly preferred aryl groups are;
phenyl, 2-methylphenyl, 2-ethylphenyl, 2-isopropylphenyl, 2-tert-butylphenyl, 3-pentylphenol, 4-isobutylphenyl, 2,3-dimethylphenyl, 2,4,6-trimethylphenyl, 2-(2-dimethylaminoethyl)-phenyl, 2-trifluoromethylphenyl, 4-(2-hydroxyethyl)-phenyl, 3-vinylphenyl, 4-(propionyl)-phenyl, 4-benzoylphenyl, 2-chlorophenyl, 3-fluorophenyl, 2-methoxyphenyl, 3,4-dimethoxyphenyl, 4-benzyloxyphenyl, 1-naphthyl, 2-naphthyl and 2-indenyl.

Particularly preferred hetaryl groups are:
pyridyl, pyrimidyl, pyrazolyl, imidazolyl, thienyl, furyl, oxazolyl and indolyl, suitable substituents being those which have been given above for particularly preferred aryl groups.

Particularly preferred cyclo-$C_4$–$C_{12}$-alkyl ketones are:
cyclobutanone, cyclopentanone, cyclohexanone, 4-methyl-cyclohexanone, 2-methyl-cyclohexanone, 2-tert-butyl-cyclohexanone, 4-tert butyl-cyclohexanone, cyclohexanone and 2,4,4-trimethyl-2-cyclohexanone.

Bases which may be used in the process according to the invention are, for example, hydroxides or alkoxides of alkali metals or quaternary ammonium hydroxides. These are, in particular, lithium, sodium or potassium hydroxides, lithium, sodium or potassium $C_1$–$C_4$-alkyl alkoxides or tetra-$C_1$–$C_4$-alkylammonium hydroxides. Particular preference is given to potassium hydroxide, lithium hydroxide, potassium methoxide, sodium methoxide, sodium isopropoxide, potassium tert-butoxide, tetramethylammonium hydroxide and tetrabutylammonium hydroxide.

For the preparation of the catalyst of the formula (I), suitable diamines are those which can form a chelate complex with Ru(II). For example, mention may be made of: 1,2-diaminoethane, 1,2- and 1,3-diaminopropane, 1,2-diaminobutane, 2,3-diaminobutane, 2,3-diaminopentane, 1,2-diamino-1,2-diphenylethane, 1,2-diaminocyclopentane, 1,2-diaminocyclohexane, 1,2-diamino-methyl-cyclohexane, 1-amino-2-N-methylamino-ethane and 1-amino-1-methyl-2-N-methylaminocyclohexane.

Preferred optically active amines for the preparation of the support-bonded catalysts of the formula (I) are chirally uniform diamines, in particular those derived from 1,2-diaminoethane and from 1,2-diaminocyclohexane and can contain, as substituents, optionally $C_1$–$C_8$-alkyl, $C_4$–$C_9$-cycloalkyl, $C_6$–$C_{10}$-aryl-$C_1$–$C_8$-alkyl, $C_2$–$C_8$-alkenyl and/or $C_6$–$C_{10}$-aryl groups optionally substituted by $C_1$–$C_8$-alkyl and/or $C_1$–$C_8$-alkoxy.

For the preparation of the novel catalysts of the formula (I), particular preference is given to the diamines of the formulae (III) and (IVa–c):

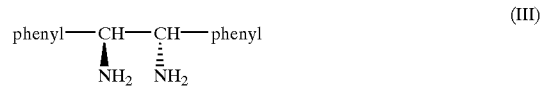

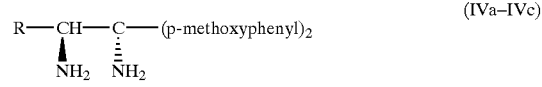

For the preparation according to the invention of optically active alcohols, these optically active amines can be used either as (S,S)-, (R,R)-, (R)- or (S)-stereoisomers.

These stereoisomers can be prepared in a known manner or analogously thereto (see e.g. Tetrahedron, Lett. 34 (12), 1905 (1993). Which optically active amine in which form in combination with a certain catalyst to be used according to the invention in the preparation according to the invention of a certain optically active alcohol affords optimum results can be ascertained, if desired, by routine experimental theories in accordance with the "in situ" variant of the process.

When the process according to the invention is carried out in accordance with the "in situ variant", if the procedure is discontinuous, i.e. in a stirred autoclave, the amount of a catalyst of the formula (b), calculated as moles of Ru(II), is, per mole of carbonyl compound, in the range from 1:100 to 1:100000, and this amount is preferably 1:200 to 1:10000.

The diamine can, based on heterogeneous Ru(II) phosphine complex catalyst(s), (calculated as moles of Ru(II)), be used, for example, in amounts of from 1:0.5 to 1:4. This amount is preferably 1:1 to 1:2.5 per mole of Ru(II). The base can, based on the heterogeneous Ru(II)-phosphine complex catalyst (calculated as moles of Ru(II)), be used, for example, in amounts of from 0.5 to 1000 equivalents. This amount is preferably 2 to 40 equivalents of base per mole of Ru(II).

If the process according to the invention is carried out using a separately isolated prepared catalyst of the formula (1), the amount of the catalyst (calculated as equivalents of Ru(H) per mole of carbonyl compound used) may be 1:100 to 1:500 000. This amount is preferably 1:1 000 to 1:200 000.

In the case of the use of catalysts of the formula (I), an addition of diamine to the reaction mixture or to the solution of the substrate is not necessary, but may be advantageous to increase the service life of the heterogeneous catalyst. The amount of such an addition of diamine is in the range from 0.01 to 1.0 equivalents, based on moles of Ru(II) complex used.

For the amounts of base used, the ratios are the same as those which have been given above for the in situ variant.

It is advantageous to carry out the process according to the invention in the presence of solvents. Suitable solvents are those which do not react in an undesired manner with the materials used and have sufficient solubilizing power for the carbonyl compound used and the amine used. Examples are aliphatic hydrocarbons such as hexane and isooctane, aromatic hydrocarbons such as toluene and the xylenes, halogen-containing hydrocarbons such as methylene chloride, linear and cyclic aliphatic ethers such as tert-butyl methyl ether and tetrahydrofuran, $C_1$–$C_8$-alkyl and $C_7$–$C_{10}$-aralkyl alcohols such as methanol, ethanol, n-propanol, isopropanol and benzyl alcohol and dipolar-aprotic solvents such as acetonitrile, dimethylformamide and N-methylpyrrolidone.

Preferred solvents are $C_1$–$C_4$-alkyl alcohols, in particular isopropanol, it is also possible to use solvent mixtures.

It is possible to work without the addition of solvents or with solvent additions up to below a substrate concentration of 1% by weight or less. Solvent is preferably used in an amount such that a substrate concentration in the range from 10 to 50% by weight results.

The hydrogen pressure to be applied during the process according to the invention can, for example, be between 1 and 150 bar. It is preferably in the range from 3 to 120 bar, in particular between 5 mid 100 bar.

The reaction temperature during the process according to the invention can, for example, be in the range from −20 to 120° C. It is preferably in a range from +15 to +100° C., in particular from +25 to +100° C.

The reaction time is dependent on the embodiment of the process and the reaction conditions. It is generally in a range of from, for example, 5 minutes to 12 hours.

In the process according to the invention, the work-up of the reaction mixture is simple since the catalyst can be removed, for example, by filtration and the bases and amines present in the reaction mixture can be removed with the help of an ion exchanger. The isolated catalyst can be reused. The prepared, optionally optically active alcohols are not contaminated with catalysts or constituents thereof following work-up of the reaction mixture. The process according to the invention can also be carried out continuously without problems.

Surprisingly, the process according to the invention shows selectivities and activities that are at least comparable to homogeneous catalysts.

EXAMPLE

Example 1

A Solution of 12 g of Acetophenone in 100 ml of Isopropanol with the Addition of 500 mg of a Support-bonded Ruthenium Complex of the Formula (IIa)

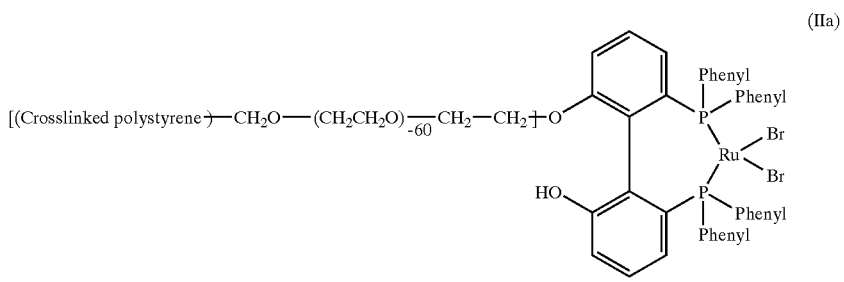

[S-Atropisomer (content of Ru: 0.21 mmol/g)]

39 mg of (S)-1,1-di-(p-anisyl)-3-methyl-1,2-diaminobutane and 420 μl of a 0.5 molar solution of potassium hydroxide in isopropanol was degassed in a 250 ml stirred autoclave a number of times under freeze-drying conditions ("freeze-thaw cycles") and the gas phase was replaced by hydrogen. Hydrogen was then injected to a pressure of 50 bar at 40° C. for 6 hours. The mixture is then filtered under a protective gas, and the reaction solution which remains was treated with an acidic ion exchanger resin, the diamine and potassium ions being bonded. After filtration, the laden exchanger resin was washed a number of times with isopropanol and the product solution, together with the wash phases, were distilled. 11.6 g of more than 99% pure 1-phenyl-ethanol with a content of 90% of R-enantiomer were obtained (CSP-HPLC analysis).

The recovered, support-bonded ruthenium complex and the diamine recovered and separated off by means of ion exchange were used in a further preparation process corresponding to Example 1 in place of fresh catalyst and fresh diamine. Virtually identical results were obtained.

Example 2

Preparation of the Ru complex used in Example 1 a) 0.5 g of (S)-6,6'-dihydroxydiphenyl-2,2'-diyl-bis-(diphenylphosphine), prepared in accordance with WO 93/15090, Example 1, were dissolved under argon in 50 ml of anhydrous and degassed tetrahydrofuran, and a suspension of 0.216 g of sodium hydride in 10 ml of dimethylformamide was added. The mixture was stirred for 60 minutes at room temperature. 4 g of TentaGel® S-bromide were then added and the mixture was stirred for a further 48 hours at room temperature. TentaGel reactive resins (products from Rapp Polymere GmbH, Tabingen, Germany) are copolymers obtained by stepwise grafting of a crosslinked polystyrene matrix with polyethylene glycol and ethylene oxide according to EP 187 391. They contain freely movable end groups, e.g., in the case of TentaGel S—Br, the group $CH_2$—$CH_2$—Br. The solid present was then filtered off, stirred with saturated aqueous ammonium chloride solution and then with 3×50 ml of anhydrous methanol and filtered. After the last filtration, the resulting product was dried under reduced pressure.

b) 800 mg of the modified support resin obtained according to a) and 53 mg of bis-(2-methallyl)-cyclooctane-1,5-diene-Ru(II). complex were suspended under argon in 20 ml of anhydrous and degassed acetone and dissolved with stirring. 1.38 ml of 0.29 molar hydrogen bromide solution were then added. The mixture was stirred for 2 hours at room temperature, then filtered under argon. The solid obtained was washed under argon with acetone, then with isopropanol, until the filtrate was free from ruthenium.

After drying under reduced pressure, a ruthenium analysis revealed a loading of 0.21 mmol/g.

Example 3

A solution of 12 g of acetophenone in 100 ml of isopropanol with the addition of 40 mg of a support-bonded ruthenium complex of the formula (Ia)

Example 4

Preparation of the catalyst of the formula (Ia) used in Example 3

1 g of the catalyst of the formula (IIa) prepared as in Example 2 was added, under argon, to a degassed solution of 120 mg of (S)-1, 1-di-(p-anisyl)-3-methyl-1,2-diaminobutane in 20 ml of dichloromethane, and the mixture was kept at 25° C. with stirring for 12 hours. After filtration under a protective gas, the resulting catalyst of the formula (Ia) was washed with 20 ml of dichloromethane and then dried under reduced pressure.

Example 5

A total quantity of 30 g of the heterogeneous bisphosphine-diamine-Ru complex catalyst obtained according to Example 11—which had been filled in equal quantities under argon into three sealed-off glass ampoules—was introduced into three stirred autoclaves which were connected to form a stirred vessel cascade having an effective total volume of 1.5 l and each contained an overflow shut off by sintered metal frits having a pore size of 10 μm.

After filling the apparatus, which had previously been purged with argon, with pure 2-propanol and introducing hydrogen under a pressure of 10 bars the stirrers were set in operation (the glass ampoules having been broken open and the catalyst suspended) and at the same time a solution of 20 g of 1-acetylnaphthalene (1'-acetonaphthone) in 250 ml of 2-propanol, to which 2.3 ml of a 1.0 M potassium tert.-butylate solution in tert.-butanol had also been added, was pumped in continuously per hour.

The reaction temperature was kept at 25° C.

Analytical examinations (by GC and CSP-HPLC) of samples obtained after specific operating periods of the hydrogenation apparatus, revealed for the hydrogenation product [1-(α-naphthyl)-ethanol] a conversion rate of 98% and an enantioselectively of 97% ee after 10 hours of continuous operation, a conversion rate of 100% and an enantioselectively of 98% ee after 100 hours of continuous operation and a conversion rate of 99% and an enantioselectively of 98% ee after 240 hours of continuous operation.

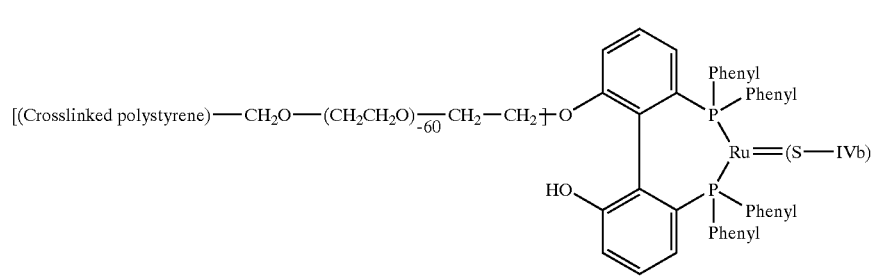

(Ia)

[S-Atropisomer (content of Ru: 0.20 mmol/g)]
and of 420 μl of a 0.5 molar solution of potassium hydride in isopropanol was degassed in a 250 ml stirred autoclave a number of times under freeze-drying conditions ("freeze-thaw cycles"), and the gas phase was replaced by hydrogen. Hydrogenation was then carried out with stirring at 40° C. at a hydrogen pressure of 40 bar for 2 hours. Following filtration and washing out of the catalyst which remains as filter residue using 10 ml of isopropanol, the filtrate, combined with the wash solution, was distilled under reduced pressure, giving 11.7 g of pure 1-phenyl-ethanol with a content 90% of R-enantiomer (CSP-HPLC analysis).

Example 6

4.0 g of (S)-(6,6'-dihydroxybiphenyl-2,2-diyl)bis (diphenylphosphine oxide), 3.65 g of potassium carbonate and 5.8 g of cyclohexyl bromide were added to 70 ml N,N-dimethylformamide, and the mixture was stirred over a period of 60 h at 80° C. After cooling the unchanged (S)-(6,6'-dihydroxybiphenyl-2,2'-diyl)bis (diphenylphosphine oxide), (3.2 g) and inorganic salts were filtered off: 100 ml of water were added to the clear solution of the product and then the mixture was extracted three times with 30 ml of chloroform. The separated organic phase was dried ($Na_2SO_4$), concentrated on a rotary evaporator and the raw product was purified by chromatography, (silica gel Merck 60, eluent:ethyl acetate/methanol/water 75:3:1.5). 700 mg of pure (S)-(6-cyclohexyl)-oxy-6'-hydroxybiphenyl-2,2'-diyl)bis(diphenylphosphine oxide) were obtained, Fp. 159–162°, $[\alpha]_D 98.7°$ (c=1.7, $CHCl_3$.

Example 7

280 mg of (S)-(6-cyclohexyloxy-6'-hydroxybiphenyl-2,2'-diyl)bis(diphenylphosphine oxide), 260 mg of potassium carbonate and 0.2 ml of bromoacetic acid methylester were added to 10 ml N,N-dimethylformamide. The mixture was stirred over a period of 12 h at 80° C. After cooling 30 ml of water were added to the mixture. Then the mixture was extracted three times with 30 ml of chloroform. The separated organic phases were combined and dried ($MgSO_4$) and concentrated on a rotary evaporator. After flash chromatography on silica gel 291 mg of (S)-(6-cyclohexyloxy-6'-methoxycarbonylmethoxybiphenyl-2,2'-diyl)bis(diphenylphosphine oxide) were obtained. $[\alpha]_D=68.1°$ (c=1.1, $CHCl_3$).

Example 8

4.0 g of (S)-(6-cyclohexyloxy-6'-methoxycarbonylmethoxybiphenyl-2,2'-diyl)bis-(diphenylphosphine oxide), (product prepared analogous to example 7), were solved in 50 ml of dried THF. The methyl Grignard reagent prepared from 310 mg of magnesium turnings and 1.76 g of methyl iodide in THF (80 ml) was added over 30 minutes using a dropping funnel. Then the stirred mixture was heated at 50° C. for 8 h. After cooling 250 ml of water were added and then the mixture was acidified with 2N hydrochloric acid and extracted with chloroform (50 ml) three times.

The separated organic phases were combined, dried ($Na_2SO_4$) and concentrated on a rotary evaporator. The product was purified by chromatography, (silica gel Merck 60, eluent: ethyl acetate/methanol/water 75:3:1.5). Yield: 3.7 g of (S)-[6-cyclohexyloxy-6'-(2-hydroxy-2-methylpropyloxy)biphenyl-2,2'-diyl]bis(diphenylphosphine dioxide).

Example 9

3.70 g of (S)-[6-cyclohexyloxy-6'-(2-hydroxy-2-methylpropyloxy)biphenyl-2,2'-diyl]bis(diphenylphosphine dioxide) were added to 75 ml of acrylonitrile. 10 ml of conc. sulphuric acid were added to the cooled and stirred solution at 0°-5° over a period of 30 minutes using a dropping funnel. Then the mixture was stirred for 5 h at 25° C. After cooling to 0° C. 300 ml of water were added and then the mixture was extracted with chloroform (each 100 ml) three times. The separated organic phases were combined, dried ($Na_2SO_4$) and concentrated on a rotary evaporator. The product was purified by chromatography (silica gel Merck 60, eluent:ethyl acetate/methanol/water 75:3:1.5). Yield: 3.3 g of (S)-[6-(2-acrylamido-2-methylpropyloxy)-6'-cyclohexyloxybiphenyl-2,2'-diyl]bis(diphenylphosphine oxide).

Example 10 a) 30 g of a dried YMC-silica gel, ave. particle size 20 μm, 3 g of 3-mercaptotrimethoxysilane, 0.9 g of p-toluenesulphonic acid monohydrate and 0.2 ml of water were added to 300 ml of toluene and the mixture was stirred over a period of 8 h at reflux temperature. After cooling the modified silica gel was filtered and washed with $CH_2Cl_2/CH_3OH$ (1:1), two times with $CH_2Cl_2$ and finally it was dried under a high vacuum at 40° C.

yield: 31.8 g analysis: S-content: 1.2%.

b) 30 g of the modified silica gel, obtained like described in example 10 a, 3 g of (S)-[6-(10-N-methacryloylamido-decyloxy)6'-cyclohexyloxybiphenyl-2,2'-diyl]bis(diphenylphosphine oxide), 3 g styrene (fresh distilled) and 60 mg of AIBN were added to 50 ml of toluene. The mixture was stirred over a period of 12 h at 60° C. then 0.4 g of 2,2-methylene-bis(6-tertbutyl-4-methylphenol) and 3 ml of bistrimethylsilylacetamide were added and the mixture was stirred at 100 over a period of 4 h. After cooling the grafted silica gel was filtered and washed after each other with—each 30 ml—of $CH_2Cl_2$, $CH_2Cl_2/CH_3OH$ (1:1), toluene, isopropanol and again with $CH_2Cl_2$. The grafted silica gel was then dried under a high vacuum at 40° C., yield: 34.4 g analysis: P-content: 0.3% corresponding to 0.050 mmol diphosphinoxide/g silica gel.

30 g of the modified silica gel, obtained like described in example 10 b, 15.50 ml of tributylamine and 3.85 ml of trichlorosilane were added under argon atmosphere to 100 ml of xylene. The resulting was stirred at reflux temperature for 24 h. After cooling to room temperature the silica gel was filtered (all operations under argon). Then the silica gel was suspended in 100 ml of dichloromethane and to the stirred mixture 30 ml of 4 N sodium hydroxide aqueous solution were added. This mixture was stirred over a period of 1 h at room temperature. Then the silica gel was filtered again and washed with each 100 ml of dichloromethane/methanol (1:1), toluene, isopropanol and finally with dichloromethane. The modified silica gel was dried under a high vacuum at 40° C. yield 29.7 g.

analysis: P-content: 0.32% corresponding to 0.051 mmol diphosphine/g silica gel.

Example 11

29.7 g of the silica gel, obtained like described in example 10c, and 1.176 g $[RuCl_2(\eta^6\text{-benzene})]$ (=2.35 mmol) were added under, argon to 150 ml of degassed DMF. Then the stirred mixture was heated at 80° C. for 24 h. After cooling to 25° C. the solution phase was removed using a cannula fitted with a membrane with pores (<20 μm) and then the silica gel was rinsed five times with DMF (100 ml).

Then 2.425 g (=11.42 mmol) of (S,S)-1,2-diphenylethylenediamine, solved in 150 ml of degassed DMF, were added and the stirred mixture was heated at 80° C. for 24 h. After cooling the silica gel was filtered and washed seven times with DMF (50 ml) and seven times with dichloromethane (50 ml). Then the immobilized catalyst was dried under a high vacuum at 40° C. for 12 h, yield: 30.0 g

Example 12 a) 3.35 g of (S)-(6-cyclohexyloxy-6'-hydroxybiphenyl-2,2'-diyl)bis(diphenylphosphine oxide), (prepared analogous to example 6), 2.0 g of N-(10-bromo decyl)phthalimide and 3.2 g of potassium carbonate were added 70 ml of N,N-dimethylformamide and the mixture was stirred for 60 h at 80° C. After cooling 100 ml of water were added and the mixture was extracted three times with 30 ml of chloroform. The separated organic phases were combined, dried ($Na_2SO_4$) and concentrated on a rotary evaporator. Analogous to the known Gabriel synthesis of amines the obtained raw product (4.8 g) was transformed into the (S)-[6-(10-aminodecyloxy)-6'-cyclohexyloxybiphenyl-2,2'-diyl]bis-(diphenylphosphine oxide) by treatment with hydrazine hydrate, hydrochloric acid and finally with aqueous sodium hydroxide. After purification by chromatography, (silica gel Merck 60, eluent:ethyl acetate/methanol/water 75:3:1.5), the yield of pure product was 3.2 g.

b) The obtained pure product (3.2 g) was dissolved in 100 ml of chloroform and 0.6 g of triethylamine were added to the solution. 0.4 g of methacryloyl chloride, dissolved in 10 ml of chloroform were added, using a dropping funnel, to the stirred and cooled (0°–5° C.) solution over a period of 20 minutes. Then the mixture was stirred for 6 h at room temperature. The mixture was concentrated on a rotary evaporator, 100 ml of chloroform were added and the mixture was extracted with 50 ml of aqueous 2N HCl and 50 ml of water. The organic phase was separated, dried ($Na_2SO_4$) and concentrated on a rotary evaporator. The product was purified by flash chromatography. Yield 3.0 g of (S)-[6-(10-N-methacryloylamido-decyloxy)-6'-cyclohexyloxybiphenyl-2,2'-diyl]bis(diphenylphosphine oxide).

What is claimed is:

1. A Ru(II) complex catalyst containing a support-bonded bisphosphine ligand and a diamine ligand.

2. A process for the preparation of non-chiral or optically active alcohols comprising reacting a carbonyl compound with hydrogen in the presence of a catalyst, a base, and optionally a diamine, wherein the catalyst is a Ru(II) complex catalyst according to claim 1.

3. A process according to claim 2 wherein the catalyst is formed in situ from a support-bonded catalyst precursor and a diamine.

4. A process according to claim 2 wherein the catalyst contains a chirally uniform, support-bonded bisphosphine ligand and a chirally uniform diamine ligand.

5. A process according to claim 4 wherein the bisphosphine ligand is an atropisomeric bisphosphine ligand.

6. A process according to claim 2 wherein the bisphosphine ligand is bonded to the support by linking functional groups of the bisphosphine ligand with reactive groups on the support or on a spacer attached to the support.

7. A Ru(II) catalyst obtained by linking an inorganic support containing SH groups with a bisphosphine or derivative thereof capable of polymerization.

* * * * *

UNITED STATES PATENT AND TRADEMARK OFFICE
CERTIFICATE OF CORRECTION

PATENT NO. : 6,787,676 B2
DATED : September 7, 2004
INVENTOR(S) : Arlt, Dieter

It is certified that error appears in the above-identified patent and that said Letters Patent is hereby corrected as shown below:

Column 6,
Line 32, "formula $M^3$" should read -- formula $M^2$ --.

Column 7,
Line 32, "$BrCH_2COOR^3$" should read -- $BrCH_2COOR^1$ --.
Lines 48-49, "tractional crystallization" should read -- fractional crystallization --.

Lines 60-61, "$M^{10}$ and $M^9$" should read -- $M^{10^1}$ and $M^{9^1}$ --.

Column 8,
Line 35, "$M^9$ or $M^{10}$" should read -- $M^{9^1}$ or $M^{10^1}$ --.

Line 62, "for examples" should read -- for example --.

Column 9,
Line 13, "$C_2 - C_{12}$-alkenyl or $C_2 - C_{12}$-alkenyl" should read
-- $C_2 - C_{12}$-alkenyl or $C_2 - C_{12}$-alkinyl --.
Line 17, "alkenyl, alkenyl" should read -- alkenyl, alkinyl --.
Line 19, "($C_6$" should read -- $C_6$ --.
Line 25, "halogen-$C_1$-$C_{12}$ alkyl" should read -- halogeno-$C_1$-$C_{12}$-alkyl --.
Line 26, "halogen" should read -- halogeno --.
Lines 26-27, "halogen-$C_1 - C_{12}$-alkoxy" should read -- halogeno-$C_1 - C_{12}$-alkoxy --.

Signed and Sealed this

Seventeenth Day of January, 2006

JON W. DUDAS
*Director of the United States Patent and Trademark Office*